United States Patent
Mitidis et al.

(10) Patent No.: US 11,270,800 B1
(45) Date of Patent: Mar. 8, 2022

(54) SPECIALIZED HEALTH CARE SYSTEM FOR SELECTING TREATMENT PATHS

(71) Applicant: Aptima, Inc., Woburn, MA (US)

(72) Inventors: Andonis Mitidis, Rogers, AR (US); Jeanine Ayers, Gibsonia, PA (US)

(73) Assignee: Aptima, Inc., Woburn, MA (US)

( * ) Notice: Subject to any disclaimer, the term of this patent is extended or adjusted under 35 U.S.C. 154(b) by 0 days.

(21) Appl. No.: 16/186,278

(22) Filed: Nov. 9, 2018

Related U.S. Application Data

(60) Provisional application No. 62/583,810, filed on Nov. 9, 2017.

(51) Int. Cl.

| | |
|---|---|
| *G16H 50/70* | (2018.01) |
| *G16H 10/60* | (2018.01) |
| *G16H 50/20* | (2018.01) |
| *G16H 50/30* | (2018.01) |
| *G16H 80/00* | (2018.01) |
| *A61B 5/00* | (2006.01) |

(52) U.S. Cl.
CPC ............ *G16H 50/70* (2018.01); *G16H 10/60* (2018.01); *G16H 50/20* (2018.01); *A61B 5/4842* (2013.01); *G16H 50/30* (2018.01); *G16H 80/00* (2018.01)

(58) Field of Classification Search
CPC ........ G16H 50/70; G16H 10/60; G16H 50/20; G16H 50/30; G16H 80/00; A61B 5/4842
USPC ............................................................ 705/2
See application file for complete search history.

(56) References Cited

U.S. PATENT DOCUMENTS

| | | | |
|---|---|---|---|
| 2010/0305961 A1* | 12/2010 | Broder | G16H 40/63 705/2 |
| 2014/0058755 A1* | 2/2014 | Macoviak | G16H 10/60 705/3 |
| 2014/0141983 A1* | 5/2014 | Singh | A61K 39/3955 506/7 |
| 2016/0110523 A1* | 4/2016 | Francois | G16H 10/60 705/2 |
| 2017/0091423 A1* | 3/2017 | Kumar | G16H 20/70 |
| 2019/0274554 A1* | 9/2019 | Yoon | G16H 50/70 |
| 2020/0395129 A1* | 12/2020 | Kalkstein | G16H 50/20 |

OTHER PUBLICATIONS

Ableson, A. (2006). Inferring interpretable pattern-based classification models from data using frequent pattern discovery algorithms and maximum entropy probability distributions (Order No. NR18493). Available from ProQuest Dissertations and Theses Professional. (304965343) (Year: 2006).*

(Continued)

*Primary Examiner* — Christopher L Gilligan
*Assistant Examiner* — Bennett Stephen Erickson
(74) *Attorney, Agent, or Firm* — John J. Brooks, III

(57) ABSTRACT

Methods for selecting treatment paths are disclosed generally comprising the steps of: (a) discovering a set of treatment path clusters based on latent patterns in historical patient trace data, (b) building a set of binary classifiers based on historical patient trace data, historical patient data and target outcomes, and (c) given the treatment path clusters, actual patient data, and a selected target outcome, applying the binary classifiers to predict a treatment path for a new patient that optimizing the selected target outcome. Processor based systems to implement the methods are also disclosed.

17 Claims, 10 Drawing Sheets

(56) References Cited

OTHER PUBLICATIONS

Huang, Z. & Dong, W. & Ji, L. & Gan, C. & Lu, X. & Duan, H, "Discovery of Clinical Pathway Patterns from Event Logs using Probabilistic Topic Models", Journal of biomedical informatics. 2013, US, 19 pgs.

Huang, Z. & Lu, X. & Duan, H., "Latent treatment pattern discovery for clinical processes.", Journal of Medical Systems. 2013, US, 11pgs.

Blei, Davis et al., "Latent Dirichlet Allocation.", Journal of Machine Learning Research 3 (2003) 993-1022, 30 pgs.

* cited by examiner

```
•d5 = [["ARR",1],["PRE_OP",1],["PRE_OP",1],["ADMIT",2],["HICK_INS",2],["CHEMO",2],
•["CHEMO",2],["CHEMO",2],["CHEMO",2],["CHEMO",2],["BMT",3],["BMT_ADM_POST",4],
•["HOSP_DIS",5],["BLOOD_SAM",5],["ANTIBIOTIC",5],["FUP_HOSP",5],["BLOOD_SAM",5],
•["CHEMO",5],["ROUTINE_TESTS",5],["CHEMO",5],["BLOOD_TRANS",5],
•["ROUTINE_TESTS",5],["FUP_HOSP",5],["DEP",6]]
```

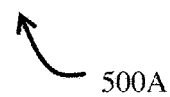

FIG. 5A

```
# Import packages

Import parameters from the params file

Define the 'unique function': function that keeps only unique words (Vocabulary)

Load data of m-many rows function # Create the Vocabulary function, U: Find the unique "words" in a corpora

Define the 'create_action_array' from corpora 'corp' with Vocabulary U function

Define the 'epoch_corpora_array' from corpora 'corp' function

Define the 'demo_data_array' from corpora 'corp' function

Load the training data from the disease_data.py

Load the demographic data from the disease_data.py

Load the test data from the disease_test_data.py

Create the Vocabulary array (U: treatment actions, V: demo features)

Create action and epoch arrays for training

# Create action and epoch arrays for test or prediction
```

FIG. 5B

SPECIALIZED HEALTH CARE SYSTEM FOR SELECTING TREATMENT PATHS

CROSS-REFERENCE TO RELATED APPLICATIONS

This application claims benefit of U.S. Pat. App. No. 62/583,810 filed on Nov. 9, 2017 and the entire content of which is herein incorporated by reference.

STATEMENT REGARDING FEDERALLY SPONSORED RESEARCH OR DEVELOPMENT

This invention was made with Government support under contract W81XWH-14-C-0021 awarded by the U.S. Army. The Government has certain rights in the invention.

REFERENCE TO SEQUENCE LISTING, A TABLE, OR A COMPUTER PROGRAM LISTING COMPACT DISC APPENDIX

Not Applicable

BACKGROUND OF THE INVENTION

1. Field of the Invention

This invention relates to medical informatics, in particular utilizing clustering and probabilistic techniques to identify optimum treatment paths given a selected outcome target.

2. Description of the Prior Art

Techniques used in this solution are related to Latent Dirichlet Allocation (LDA) by David M. Blei and an extension of it called Clinical Pathway model (CPM) by Zhengxing Huang. These disclose methods of extracting "topics" from a corpus.

In one current view of providing treatment to patients, treatment centers such as hospitals follow clinical treatment paths or patient traces that are characterized by a sequence of treatments or clinical activities recommended by a physician. Clinical treatment paths are standardized, evidence-based management plans based off of collective knowledge about how a homogenous patient group reacts to a set of care processes. It may be best if the physicians take into account the prior history of the patient, demographic data, disease stage, symptoms, patients' reactions to treatment and a set of other numerous factors in order to determine how the patient may react to the standardized care map. However, humans cannot create associations among hundreds of thousands of data, extract patterns and use that extracted information to change the standardize care map in minor or major ways to improve the outcome or to recommend a treatment path.

The disclosed solution addresses shortcomings found in existing solutions by trying to solve the problem of optimizing the treatment recommendations by physicians so that the treatment meets desired outcomes.

The solution builds on the disclosures of: (a) Latent Dirichlet Allocation (LDA) by David M. Blei at http://www.cs.columbia.edu/~blei/papers/BleiNgJordan2003.pdf ("Blei"), and (b) Clinical Pathway Model (CPM) by Zhengxing Huang at http://www.sciencedirect.com/science/article/pii/S1532046413001445 ("Huang"). Both Blei and Huang references are herein incorporated by reference in their entirety.

These disclosures describe methods of extracting treatment topics from historical treatment data of patients and clustering the patients according to the "topic content" of each patient. Blei describes "topic extraction" methods and Huang describes "clustering" methods suitable for use with some of the embodiments described herein. The LDA of Blei is a generic topic extraction analysis (not dependent on treatments). Blei does not include the time component in the topic extraction. Huang is an extension of the Blei paper such that it includes the time component and it is also an application to treatment topic extraction from medical data.

In general, Blei describes the use of LDA and Huang describes the application of LDA to clinical pathways. However, these papers have not considered time in topic extraction and they have not extended the use of this type of cluster information to help health care providers select treatment paths based on a desired outcome.

BRIEF SUMMARY OF THE INVENTION

The following summary is included only to introduce some concepts discussed in the Detailed Description below. This summary is not comprehensive and is not intended to delineate the scope of protectable subject matter, which is set forth by the description below and the claims presented at the end.

The systems and methods create "treatment path clusters" to identify the distinct groupings of clinical treatment paths to be applied to patients. The treatment paths and treatment path clusters may be statistically determined from historical treatment paths, or patient traces. Historically, every patient follows a patient trace and clusters from this historical patient trace data represent treatments that can be used alone or probabilistically grouped to be applied to future patients.

In one example embodiment, a specialized health care system for selecting a treatment path for a patient is provided, the system comprising an input device to receive historical patient trace data and patient data, a pattern extractor module configured to extract treatment patterns from the historical patient trace data, a cluster maker module configured to create one or more treatment path cluster given the historical patient trace data and the treatment patterns, a centroid maker module configured to create one or more treatment path cluster centroid from the one or more treatment path cluster, a binary classifier module configured to define and train a binary classifier, and a target outcome maximizer module configured to select the treatment path cluster centroid as the selected treatment path for the patient given a new patient data, the one or more treatment path cluster centroid, the binary classifier and a target outcome.

In some example embodiments, a specialized health care system for selecting a treatment path for a patient is provided, the system comprising a processor, a first input device to receive historical patient trace data corresponding to past treatments activities applied to one or more patients, a data formatter module, a memory configured to receive and store the formatted historical patient trace data and a formatted historical patient data, a plurality of treatment path modules, the memory further configured to receive and store a treatment path cluster and a treatment path cluster centroid, a binary classifier module configured to receive the formatted historical patient trace data, one or more target outcomes and the historical patient data to define and train a binary classifier, the memory further configured to receive and store the binary classifier, a target outcome maximizer configured to receive the treatment path cluster centroids, the new patient data and the binary classifier to select the treatment path cluster centroid as the selected treatment path for the patient and a user interface to present the selected treatment path.

In some embodiments, the data formatter module is configured to receive and transform the historical patient trace data into a formatted historical patient trace data, a historical patient data corresponding to the one or more patients into a formatted historical patient data, and a new patient data corresponding to a new patient into a formatted historical patient data.

In some embodiments, the plurality of treatment path modules comprises a pattern extractor module configured to extract treatment patterns from the formatted historical patient trace data, a cluster maker module configured to create one or more treatment path cluster given the formatted historical patient trace data and the treatment patterns, and a centroid maker module configured to create one or more treatment path cluster centroid.

In some embodiments, methods of using the specialized health care system are provided.

Other objects, features, and advantages of the techniques disclosed in this specification will become more apparent from the following detailed description of embodiments in conjunction with the accompanying drawings.

BRIEF DESCRIPTION OF THE SEVERAL VIEWS OF THE DRAWINGS

In order that the manner in which the above-recited and other advantages and features of the invention may be obtained, a more particular description of the invention briefly described above will be rendered by reference to specific embodiments there of which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 5A illustrates an example of the preprocessed format of treatment path data;

FIG. 5B illustrates pseudo code outlining one embodiment of an implementation to format historical patient trace data;

DETAILED DESCRIPTION OF THE INVENTION

Figure 1:
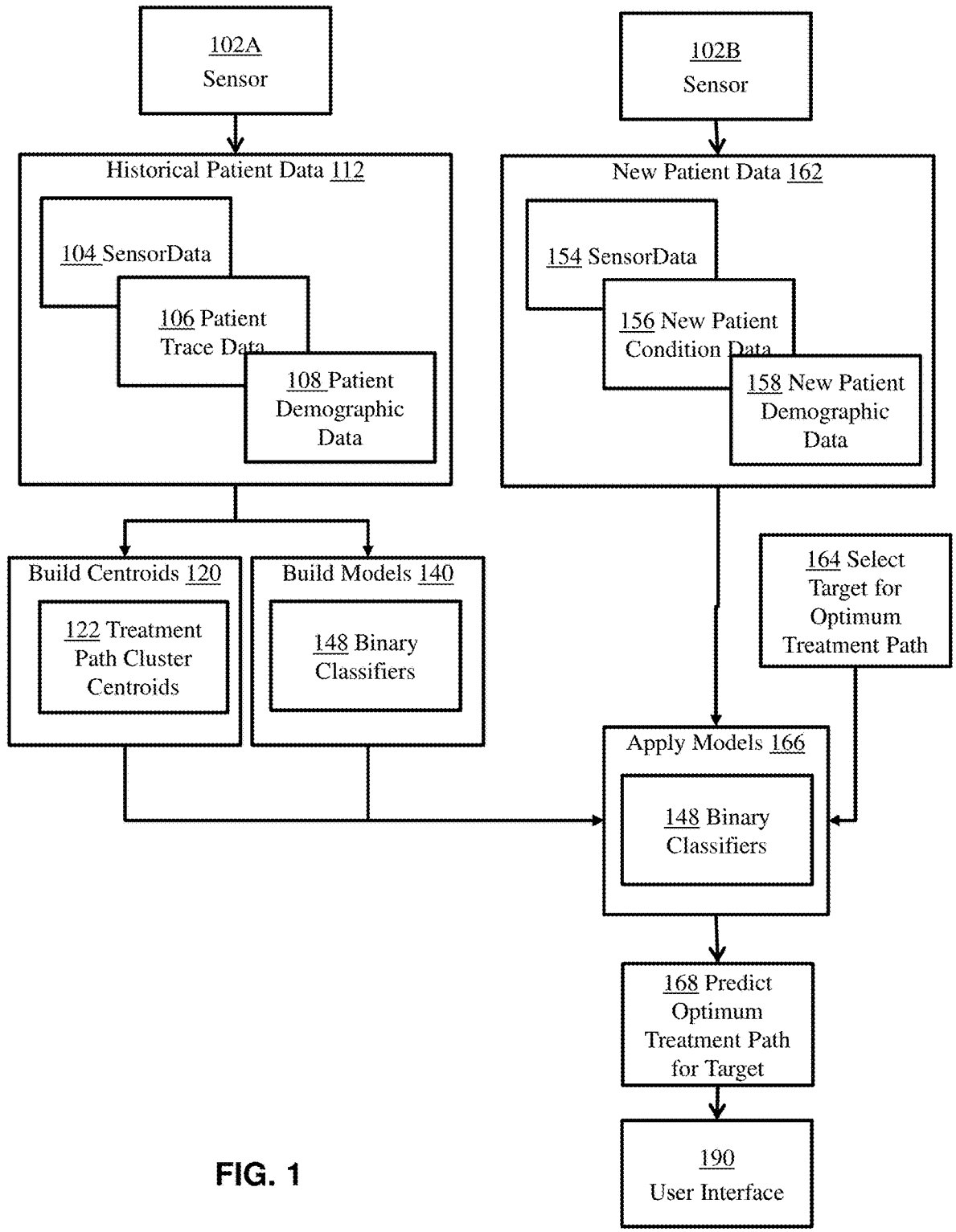
FIG. 1 shows a process diagram illustrating the general methods of one embodiment of the invention.

COPYRIGHT NOTICE: A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. The following notice applies to any software and data as described below and in the drawings hereto: Copyright © 2018, Aptima, Inc., All Rights Reserved.

Systems and methods to select treatment paths and methods of use will now be described in detail with reference to the accompanying drawings. Notwithstanding the specific example embodiments set forth below, all such variations and modifications that would be envisioned by one of ordinary skill in the art are intended to fall within the scope of this disclosure.

The systems and methods disclose utilizing "treatment path clusters" to identify the distinct groupings of clinical treatment paths that may be used to build representative treatment paths to be applied to new patients. The treatment paths and treatment path clusters may be statistically determined from historical treatment paths, or historic patient traces. Historically, every patient follows a patient trace and clusters from this historic patient trace data represent a probabilistic grouping of treatment paths that may be applied to future patients.

Even given the prior art in the field of bioinformatics, the teaching of Blei and Huang do not extend the use of this type of cluster information to help health care providers select treatment paths based on a desired outcome. One objective of the disclosed methods and systems is to accurately make recommendations on patient treatment so that physicians can optimize treatment in light of treatment targets such as the desired outcome, speed and cost of the treatment. Mathematical modeling techniques can provide a treatment path selection process that may be much faster, much more accurate and much cheaper than the current solutions.

In one embodiment of the invention, referring to the functional diagram of an example embodiment in FIG. 1, the methods generally comprise the steps of:
 a) building at 120 a set of cluster centroids 122 as potential treatment paths for new patients based on historical patient data 112 such as sensor data 104, patient trace data 106 and historical patient data 108 and treatment patterns extracted from this historical patient data 112,
 b) building at 140 a set of binary classifiers 148 based on the patient trace data 106, historical patient data 108 and desired target outcomes, and
 c) given the cluster centroids 122, actual new patient data 162, and a selected target outcome 164, applying at 166 the binary classifiers 148 to determine at 168 a treatment path for the new patient that optimizes the selected target outcome.

From the above methods, the set of treatment path clusters generally reflect the most statistically common historical treatment paths used to treat an ailment. The treatment path clusters are generally built by:
 a) given a set of treatment path data, or patient trace data for an ailment,
 b) extracting treatment topics (treatment patterns) using topic modeling methods such as "extended LDA",
 c) optimizing the number of treatment topics,
 d) clustering treatment pattern data according to their treatment topic content and optimizing the number of treatment pattern clusters, and
 e) defining cluster "centroids" as the historic "treatment paths" and potential "treatment paths" for new patients.

The result of this clustering is one or more historical treatment paths, or patient traces grouped together in clusters according to a similarity of their treatment pattern composition similarity (both in the "treatment activity" or treatment domain and also in the "time" domain). For example, a treatment path cluster will be one or more patient traces grouped together according to a similarity of treatment patterns.

The set of binary classifiers are generally used to classify, or map probabilities of patient trace data and patient data to a set of target outcomes. The binary classifiers treat data as vectors (or n-dimensional points) in an n-dimensional vector space where "n" is any integer greater than or equal to 1. By assumption, these vectors belong to one of two classes (class 1 or class 2) and the binary classifier tries to distinguish the vectors of the two classes. For example, a suitable binary classifier is a support vector machine (SVM) that draws a "hyper surface" in such a way that it splits the vector space in 2 regions, one for class 1 and the other for class 2. Therefore, when trying to predict the class of any subsequent data the binary classifier determines whether the data lies in the region for class 1 or class 2.

The binary classifiers are generally built by:
 a) receiving and formatting historical patient data,
 b) for each binary classifier, defining multiple (e.g., two) outcomes (for use later with historical patient data and treatment patterns),
 c) combining the historical patient trace data and the historical patient data to create a historical treatment path/patient data pair and associating or labelling each of the historical treatment path/patient data pair as meeting one of the two target outcomes for each classifier, and
 d) given the set of formatted historical patient trace data, related historical patient data and the labelling, training the binary classifiers on all historical trace/patient data pairs to probabilistically map historical trace/patient data pairs with one of the target outcomes.

The result of this binary classifier building is a defined probabilistic relationship between (1) the historical patient trace data, (2) historical patient data and (3) the target outcomes of each of the binary classifiers. Therefore, with a new patient data from a new patient and a defined target outcome, the treatment pattern clusters and binary classifiers are able to probabilistically map the new patient data to the treatment path cluster that will probabilistically maximize the target outcome for that patient when applied as a treatment path for the patient.

This approach goes beyond traditional approaches of defining treatment paths for patients in that:
 a) the patient data of the patient's information, for both historical and new data, is expanded so that it includes the patient's information such as demographic information and information from sensors;
 b) binary classifiers are added to define an association of historical patient data plus treatment path data to target outcomes (e.g., outcomes such as (1) positive or negative health outcome, (2) fast or slow completion of treatment and (3) inexpensive or expensive cost of treatment); and
 c) the binary classifiers are then able to be used to associate target outcomes with historic treatment paths and new patient data.

This use for binary classifiers is unconventional. A conventional use of binary classifiers trains the classifier on some data (x1, x2, . . . xn, y) and then makes predictions about a new set of data of the same format (x1', x2', . . . , xn', y'). In this illustrative example of a conventional solution: x1, x2, . . . xn are the patient data and y is the treatment path. In contrast, this unconventional specialized health care system uses the classifier to select a given y out of m-many options {y1, y2, . . . ym} as follows: we use the trained binary classifier to map all data of the form (x1, x2, . . . xn, y1), (x1, x2, . . . xn, y2), . . . , (x1, x2, . . . xn, ym) to a probability; then, holding the (x1, x2, . . . xn) fixed, the "yi" that gives the highest probability is selected as the favorable treatment path.

With the binary classifiers "trained" (with historical data), treatment path recommendations can be made as follows:
 a) When a new patient is admitted to the hospital, the new patient information of this new patient is collected and this information is combined/paired with each one of the possible treatment paths (as discovered by the clustering process).
 b) For all combinations of patient data plus treatment paths data (as created in "a"), the binary classifiers are run. Each classifier will give a percentage score for all treatment paths. For example, one score will correspond to the likelihood of positive outcome, another score will correspond to the likelihood of fast completion of treatment and another score will correspond to the likelihood of inexpensive treatment.
 c) The scores evaluated in "b" will be presented to a physician in order to provide suggestions/recommendations about what treatment path or combination of treatment paths (for that specific patient) is the optimal one according to how the physician and patient will prioritize target outcomes such as outcome, cost and speed of treatment.

The disclosed solution addresses the technical problem of how to automatically associate new patient data to historical treatment path and historical outcome data in a manner that allows for an objective and probabilistic selection of a target outcome specific to that new patient data. The technical solution to this problem is to probabilistically associate historical treatment path data, historical patient data and historical outcome data to build probabilistic relationships between these data sources. Then, the system utilizes the probabilistic relationships to relate new patient data with the historical treatment path and the target outcomes. This technical solution uniquely splits data considered into 2 parts: a patient data (part 1) that is fixed for each patient and a treatment path (part 2) (that is the physician's options) and then testing (using binary classifiers) which "part 2" should be combined with the given "part 1" in order to determine which "part 2" will give the most probable target outcome.

Additionally, the approach may be used in combination with multiple algorithms: topic/pattern extraction using (extended LDA), clustering algorithms based on the topic content and binary classifiers.

As used herein, in addition to their common definitions, the following terms will include the following meanings:
 a) A "clinical event" is a pair of a "treatment activity" identifier and the associated "time stamp". The "treatment activity" being clinical terms describing treatment activities and the "time stamp" indicating the time, time period or "epoch" at which the "treatment activity" was performed.
 b) "Cluster" shall mean one or more patient traces or historical treatment paths grouped together according to a similarity of patterns (both in the treatment activity or treatment domain and also in the time domain). For example, "treatment path cluster" shall mean one or more treatment paths grouped together according to a similarity of treatment patterns.
 c) "Clustering" is grouping of historical patient treatment paths (patient traces according to their similarities. These similarities refer to the treatment pattern composition similarity within that group of patient traces.

d) "Centroid" shall mean a treatment path probabilistically representing one or more treatment paths for a clinical pathway.
e) "Patient data" shall mean patient specific information used to describe characteristics of the patient. Patient data may include data such as sex, age, demographics, sensor data, treatment activity and general health—and may include very specific criteria such as prior, pre-existing or family health issues.
f) "Patient trace data" shall mean the historical sequence of clinical events performed on a particular patient for a clinical pathway. The patient trace data comprising both a treatment activity and a time domain when the treatment activity was performed. The term patient and inpatient are used interchangeably and mean the same thing and a historical treatment path is a historical patient trace data.
g) "Treatment pattern" shall mean the latent patterns of clinical events discovered through a probabilistic topic modeling technique such as but not limited to Latent Latent Dirichlet Allocation (LDA) or extended LDA (eLDA).
h) "Treatment path" shall mean the sequence of clinical events performed on or to be performed on a patient for a clinical pathway. The "treatment path" is a sequence of "clinical events" to be applied to the new patient. The length of one sequence may vary from the length of another sequence (since not all "treatments paths" have the same duration).

I. One Embodiment of Methods to Automatically Select Treatment Paths:

In one example embodiment, a method of selecting a treatment path for a new patient is provided utilizing binary classifiers. In this embodiment, the method comprises determining at least one treatment path cluster centroid utilizing a treatment topic extracting algorithm given (1) a historical patient trace data, and (2) a historical patient data; training a binary classifier given (1) the historical patient trace data, (2) the historical patient data, and (3) at least one outcome; applying the binary classifier to determine a probability of the outcome for each treatment path cluster centroid given (1) a new patient data, and (2) the treatment path cluster centroid; selecting one outcome as a selected outcome; and identifying the treatment path cluster centroid with the highest probability of the outcome as the selected treatment path.

Figure 2:
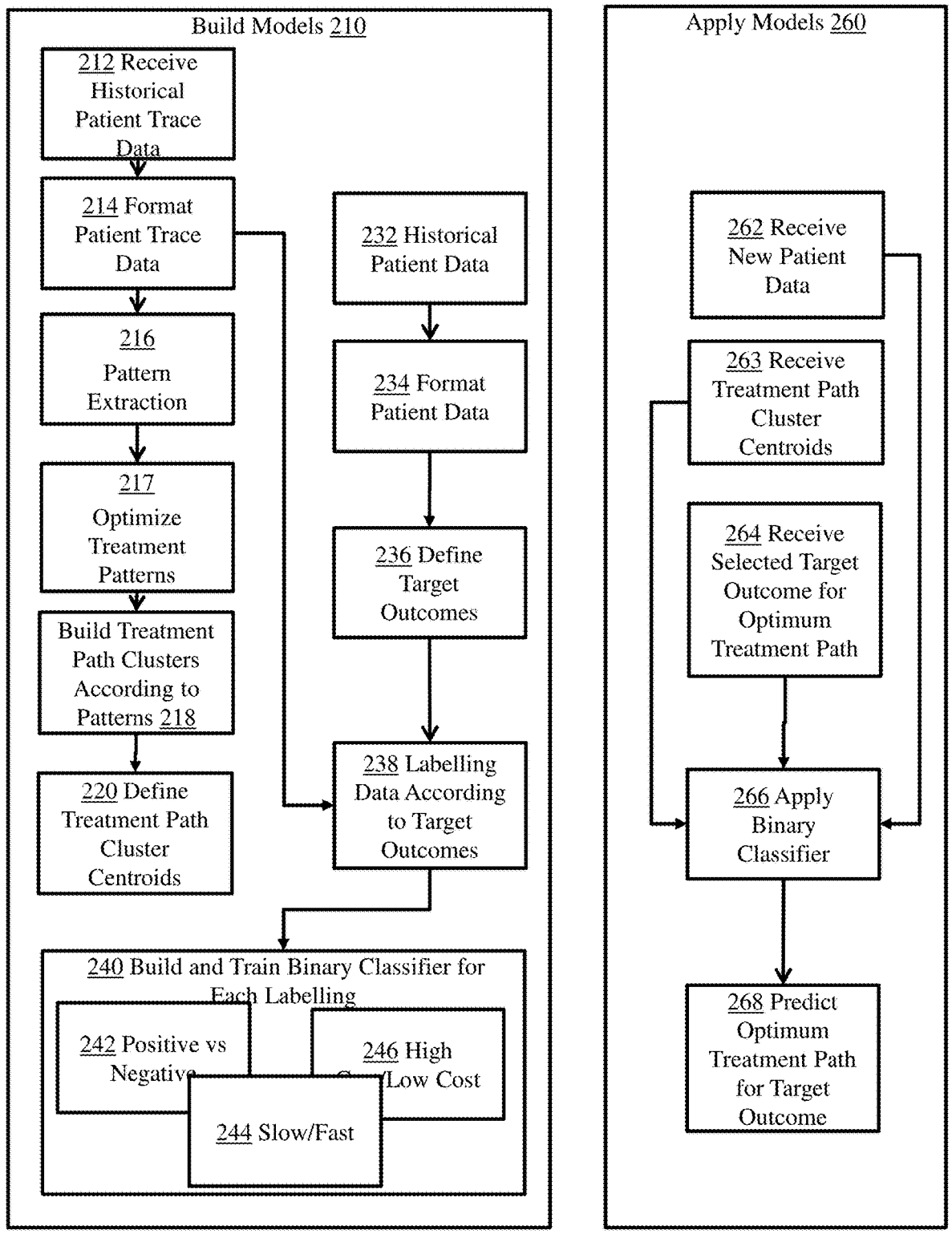
FIG. 2 shows a process diagram illustrating the general methods of one embodiment of the invention.

Referring to FIG. 2, one example embodiment of the methods to the solution generally comprise the following steps of building models with historical data at 210 and applying the models to new data at 260. The methods within these general steps are described in more detail below.

a. An Example Embodiment of Building Models

Referring to FIG. 2, one example embodiment of building models for the specialized health care system is shown at step 210. As shown at FIG. 2, at 212, historic patient trace data is received. This data is reflective of historical clinical activities, or treatment paths provided to a patient at certain times to address identified conditions or ailments. This data reflects the treatment activities provided to the patient. The raw data format may vary depending on the database of the hospital/data source.

At 214, any raw data is converted into a preprocessed format for use by the system modules. One embodiment of the preprocessed format of patient trace data is described below and an example is shown in FIG. 5A. This is the format of the input data in the topic extraction algorithm (e.g., extended LDA (eLDA)). FIG. 5B illustrates pseudo code outlining one embodiment of an implementation to format historical patient trace data.

At 216, using methods similar to those disclosed in Huang, treatment patterns are extracted using eLDA. The treatment patterns comprise underlying latent treatment patterns within the patient trace data (e.g., patient traces of Huang). The "extended" in eLDA refers to the inclusion of the time component in the Bayesian inference. The result of this step is generally a set of arrays such as:
  i. N×K array: the N-many rows correspond to the data rows and the K-many columns correspond to the treatment patterns. The data is normalized meaning that the summation along each row is equal to 1. Each column takes a number that corresponds to how similar the data is to the treatment pattern that corresponds to that particular column.
  ii. K×T array: the K-many rows of this array correspond to treatment patterns as a function of time-stamps. Each row (i.e. each topic) corresponds to a probability distribution over time-stamps. That is each row expresses the time-stamp-content of each treatment pattern.
  iii. K×(V×T) array: this consists of K-many sub-arrays, these sub-arrays represent the extracted treatment patterns. Each treatment pattern is a V×T sub-array. This sub-array can be represented as a 3-dimensional plot where one axis represents the words (or treatment activities), the other axis represents the time-stamps and the other axis (taking values from 0 to 1) represents the probability.

Array "iii" above may be plotted to visually present the treatment patterns. As shown in FIGS. 4A-4D, the arrays illustrate the action by epoch (time-stamps) and the action's probability from 0 to 1 for 4 resulting treatment patterns. Each of the figures illustrate the resulting different treatment patterns to address an ailment (e.g., clinical pathway of Huang).

Referring back to FIG. 2, at 217, the number of treatment patterns are optimized. The number of treatment patterns is a free model parameter: this means that this number is not determined by eLDA. Instead, the optimal number may be determined by the use of other criteria. One example of a suitable criteria is the "perplexity" index as defined in Latent Dirichlet Allocation (LDA) by Blei. The perplexity index has been widely used in LDA to determine the number of topics and can be defined as the reciprocal geometric mean of the likelihood of a test corpus given a model. The number of treatment patterns for which the perplexity index is minimized may correspond to the optimal number of treatment patterns.

At 218, historical treatment paths are clustered according to their treatment pattern content. For this step, all data is first expressed in its treatment path content representation and then clustering is performed using the similarity metrics (for patient trace clustering) similar to that defined in "Clinical Pathway model" (CPM) by Huang and described in more detail below.

At 220, the treatment path cluster "centroids" are discovered and defined. These centroids are the representative treatment paths of the clusters. The data clustered around each centroid generally follows (or can be described as) the representative treatment path.

At 232, patient data from historical data is received from many patients. This data is fixed for each patient and the idea is to understand what treatment paths are more suitable for each grouping of historic patient data in order to optimize the outcome.

At 234, if not formatted already, the historical patient data is formatted so that it is compatible with the format of the historic patient trace data. The historical patient data and patient trace information of each unique patient forms a new set of data that will be used in the binary classifiers. Any form of patient data is converted to a normalized numerical form. The data (like age, weight, height) that are already in numerical form we perform normalization. For the data that are in string form e.g. gender (female or male) we convert them to a zero-one array as follows: For gender we convert the data to a (1, 0) when gender=male and we use (0,1) when gender=female. If there are more choices e.g. (a, b, c) then we indicate choice b as (0,1,0), choice a as (1,0,0) and choice c as (0,0,1). Similarly, we treat all other data with more than 3 options in the same manner.

At 236, target outcomes for treatments are defined. Any type and number of target outcomes may be defined. As an example, and not for limitation, three (3) target outcomes may be defined such as: negative versus positive treatment outcomes, inexpensive versus expensive treatments, fast versus slow treatments. Different/more target outcomes may be defined as needed.

At 238, for each target outcome, a separate data labelling is performed. Each labelling is required for the training of a separate binary classifier according to outcomes. Following the example of the three target outcomes above (e.g., negative versus positive treatment outcomes, inexpensive versus expensive treatments, fast versus slow treatments) we would label each row of formatted historical treatment path/patient data pairs in three distinct ways.
  i. we label with a "0" the negative outcomes and with a "1" the positive outcomes,
  ii. we label with a "0" the expensive treatments and with a "1" the inexpensive ones, and
  iii. we label with a "0" the slow treatments and with a "1" the fast treatments.

Each one of the above three (3) labelling will be used to train a binary classifier.

At 240, multiple binary classifiers are built (trained) on all patient trace and historic patient data. For each labelling (as described above) there corresponds one binary classifier. Therefore, using the examples above, the end result will be to have a binary classifier trained to distinguish data with respect to negative versus positive outcomes, another binary classifier trained to distinguish data with respect to expensive versus inexpensive treatments and a third binary classifier trained to distinguish data with respect to slow versus fast treatments.

b. An Example Embodiment of Applying Models

Referring to FIG. 2, one example embodiment of applying models is shown at step 260. At 260, the binary classifiers are applied as part of a "prediction" subsystem that will match a new incoming patient with each one of the generic treatment patterns (treatment pattern cluster centroids) as defined in 220, depending on a selected target outcome: e.g., positive vs negative, inexpensive vs expensive or fast vs slow. These binary classifiers provide the probability that each one of the possible treatment paths, when applied to the specific patient data of the new incoming patient, will result in a desired outcome e.g. (i) a positive outcome, or (ii) inexpensive treatment, or (iii) fast treatment.

At 262, new patient data is provided. This data may be formatted to match the format of the preprocessed format of patient trace data as defined herein. The whole process described applies to a single disease or treatment type (assume to begin with). A set of initial symptoms may be defined as part of the new patient data to have the selection system analyze the patient according to the proper data and classifiers. This may also be important to define since it may reflect the severity of the disease on the day of diagnosis. If there is not much variability in the patient's symptoms then the system may be configured to ignore the symptoms (if all are indeed the same among all patients). If there is a strong variability of ("day-zero" symptoms) among patients the system may be configured to expand new patient data in order to include the initial symptoms of the disease.

At 263, the treatment path cluster centroids from step 220 are received. Each one of these centroids is combined together with the new patient data. For example if we have 5 centroids we prepare 5 sets of new patient+treatment path data (as represented by the centroids). In these sets of data, the new patient data is fixed, what changes is the centroids. The "centroids" are represented as a treatment pattern combination. For example, for cases with 4 treatment patterns we may have a centroid to be expressed as: [x1% pattern A, x2% pattern B, x3% pattern C, x4% pattern D] or simply as [x1_1, x1_2, x1_3, x1_4]; a second centroid may be represented as [x2_1, x2_2, x2_3, x2_4]; and a third centroid as [x3_1, x3_2, x3_3, x3_4]. Similarly the new patient data of a new patient may be represented as [d1, d2, d3, . . . dn]. To choose among the 3 centroids we concatenate the new patient data with the 3 centroids as follows:
  i. [d1, d2, d3, . . . dn, x1_1, x1_2, x1_3, x1_4]
  ii. [d1, d2, d3, . . . dn, x2_1, x2_2, x2_3, x2_4]
  iii. [d1, d2, d3, . . . dn, x3_1, x3_2, x3_3, x3_4]

The binary classifier will act on all 3 concatenated rows (shown above as i, ii, iii) and a probability from each action is determined. The centroid that corresponds to the highest probability corresponds to the treatment path that the patient should follow as a treatment path to maximize the likelihood for a desirable outcome. In some embodiments, in the event of a tie, it may be up to the discretion of the physician to use one treatment path versus another or a combination of both.

At 264, a target outcome is selected to define the outcome that will drive the optimum treatment path. The target outcome is one of the outcomes consistent with the outcomes/labels that have been used to train and build the binary classifiers in steps 236 and 240. The selection of the target outcome is to select which of the outcomes the user wants to maximize as an outcome.

c. An Example Embodiment of Data Preparation/Format of Patient Trace Data

Referring to FIG. 2 and the step of formatting the patient trace data 214, one example method of formatting the patient trace data is illustrated below.

Define the "patient trace data" in a "preprocessed format" as:

$$\sigma_i = \{e_1, e_2, \ldots, e_j, e_T\}$$

$$\text{where } e_1 = \{[a_1, t_1], [a_2, t_1], \ldots, [a_{N_1}, t_1]\}$$

$$e_2 = \{[a_1, t_2], [a_2, t_2], \ldots, [a_{N_2}, t_2]\}$$

.

.

$$e_T = \{[a_T, t_T], [a_T, t_T], \ldots, [a_{N_T}, t_T]\}$$

where $e_i$ is called the $i^{th}$ epoch defined by a set of "treatment activities" or actions $a_i$ and "time stamps" $t_i$ (that resemble the "time" of the $i^{th}$ "epoch"). The epoch time unit can be defined according to the problem e.g. for some diseases/ treatments it may be suitable to choose an epoch to correspond to 1 day, for some other diseases/treatments we may find it more appropriate to define the duration of an epoch as 1 week. In other instances, the epochs may not have to be of the same time duration. Each "action" may be represented in the patient trace data by an acronym e.g. $a_1$="Adm" represents "Admission", or $a_{N_T}$="Dis" represents "Discharge".

The time of each "epoch" (or "time stamp") is defined by a positive integer; e.g. $t_1=1$ represents the first day (or first hour or week), $t_2=2$ represents the second day (or second hour or week).

d. An Example Embodiment of Discovering Treatment Path Cluster Centroids

Referring to FIG. 2 and the step of discovering treatment path cluster centroids at 220, one example embodiment is illustrated below.

Each "patient trace" $\sigma_i=\{e_1, e_2, \ldots, e_j, \ldots e_T\}$ is a "document" and a set of n-many "patient trace" $\mathbb{C}=\{\sigma_1, \sigma_2, \ldots, \sigma_j, \ldots \sigma_n\}$ is a "corpora". The pattern extraction algorithm is applied on the corpora of all patient trace data. Treatment path cluster centroids (for a clinical pathway) are determined from treatment path clusters (within that clinical pathway). The treatment path clusters are determined from the treatment patterns derived from the historical patient trace data.

This process starts by extracting treatment patterns from historical treatment paths using the extended Latent Dirichlet Allocation (eLDA) algorithm. We extract K-many "treatment patterns" from this historical patient trace data. Each treatment pattern can be thought of as representing the "average" of a larger group of "patient traces". Then each patient trace is expressed as a probability distribution over the extracted treatment patterns. Note that these methods extract "treatment patterns" (also called "topics") and data (data=patient traces) is clustered based on the treatment pattern content of that data.

The clustering of the patient trace of "corpora", $\mathbb{C}$, may be preformed using a similarity metric as defined in "Clinical Pathway model" (CPM) by Huang. The number "K" of treatment patterns is a free parameter (the optimal value of K can be determined using some analysis criteria). Consistent with the clustering described in Huang, for a specific patient trace σ, the treatment pattern distribution can be defined as:

$$\vec{\theta}_\sigma = \{\hat{\theta}_{\sigma, \mathcal{Z}_1}, \hat{\theta}_{\sigma, \mathcal{Z}_2}, \ldots, \hat{\theta}_{\sigma, \mathcal{Z}_K}\}$$

where $$\hat{\theta}_{\sigma, \mathcal{Z}_i}$$

is the posterior estimate of $$\theta_{\sigma, \mathcal{Z}_i}$$

for the treatment pattern $\mathcal{Z}$ i. With this, we the similarity between two patient traces σ and σ* can be calculated as:

$$sim(\sigma, \sigma^*) = \frac{\sum_{i=1}^{K} \theta_{\sigma, z_i} \times \theta_{\sigma^*, z_i}}{\sqrt{\sum_{j=1}^{K} \theta_{\sigma, z_j}^2} \sqrt{\sum_{l=1}^{K} \theta_{\sigma^*, z_l}^2}}.$$

Figure 3:
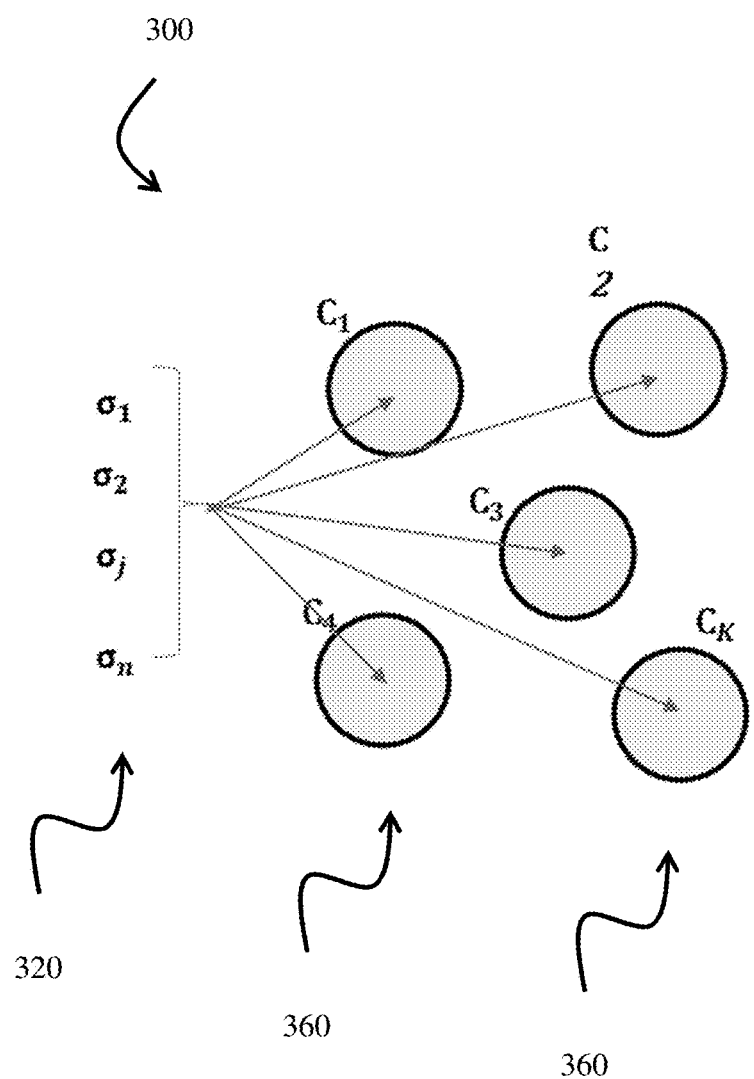
FIG. 3 illustrates the concept of obtaining clusters from treatment paths.
Figure 4A:
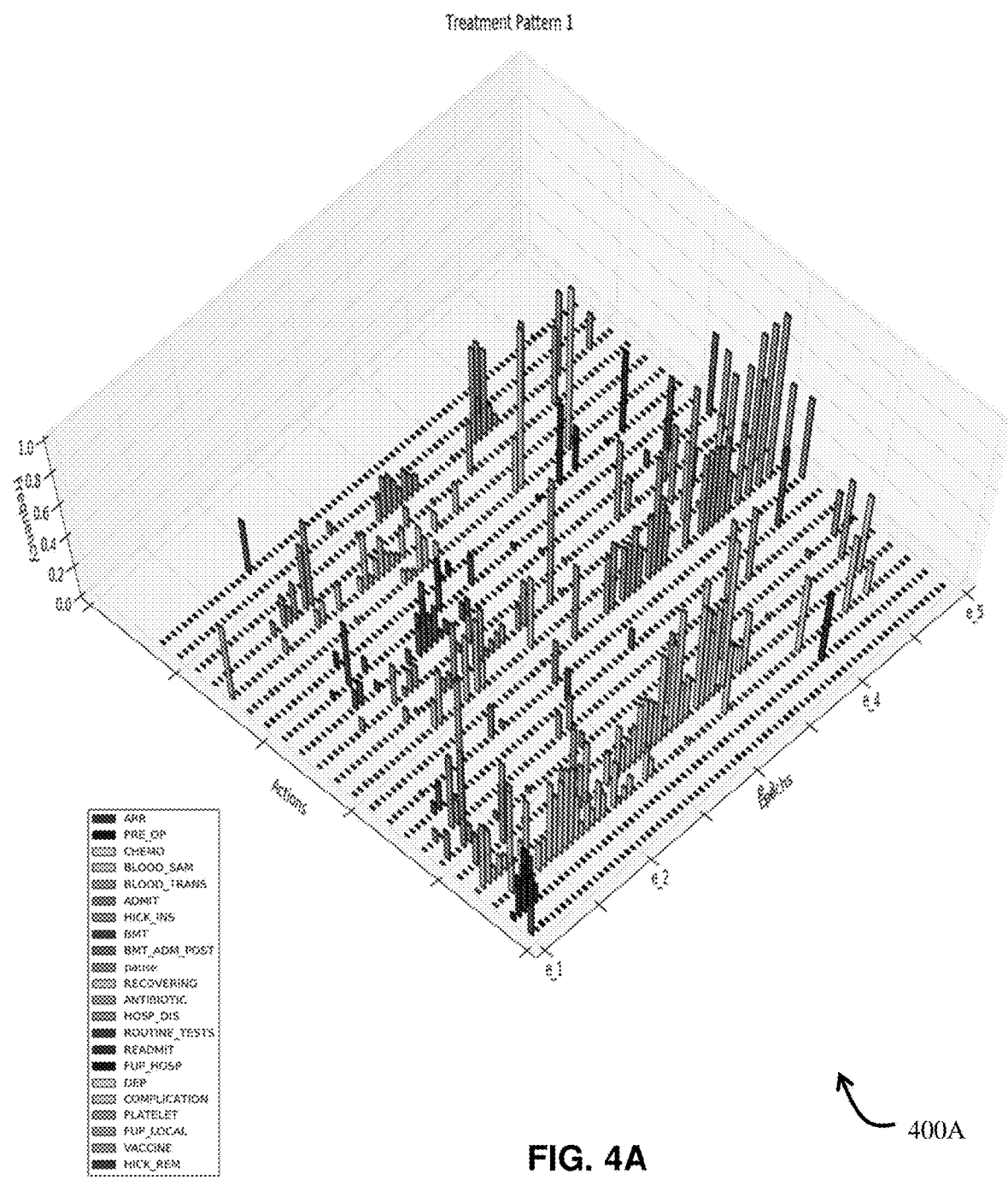
FIGS. 4A-4D illustrate sample treatment topics/patterns.
Figure 4B:
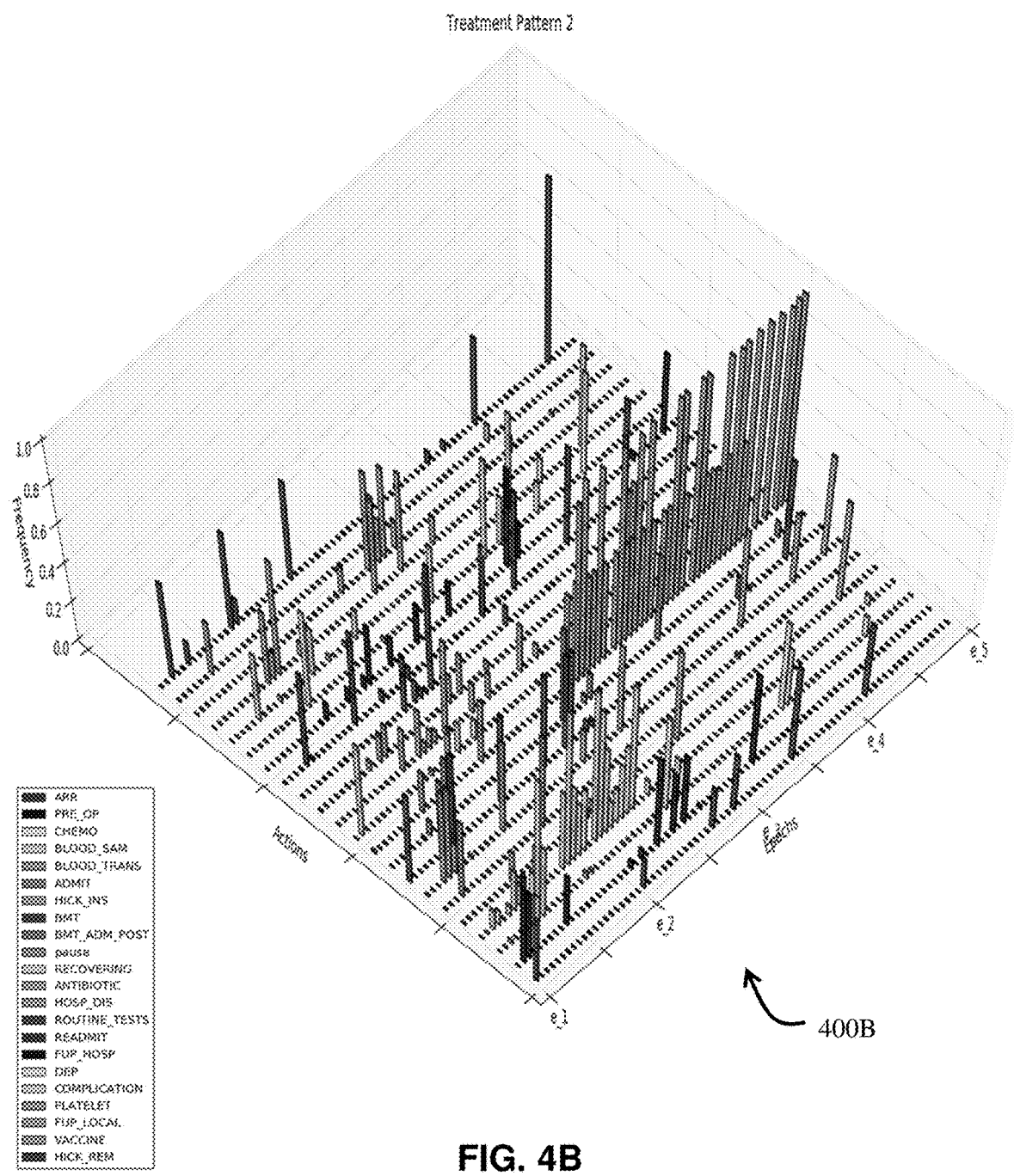
Figure 4C:
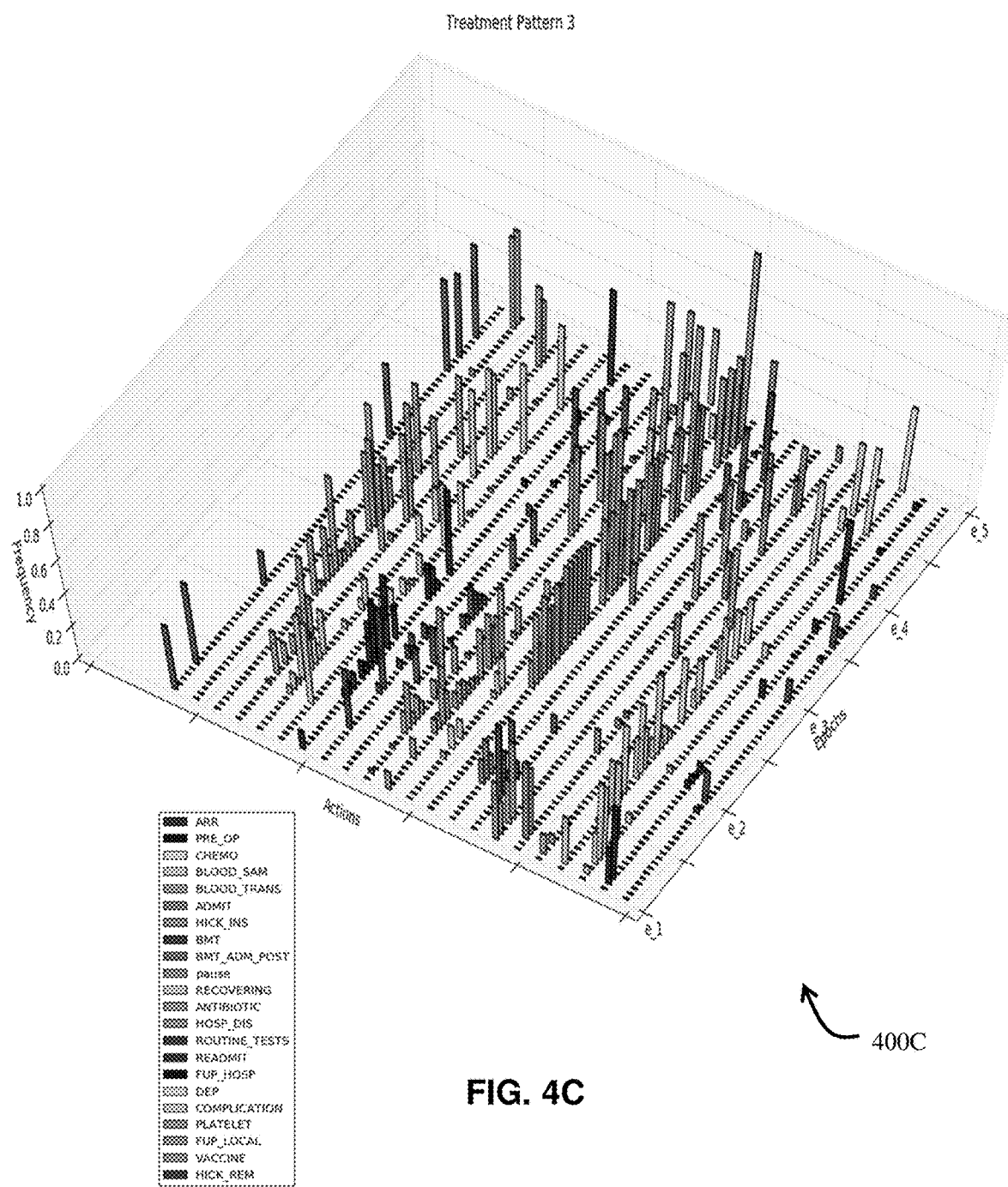
Figure 4D:
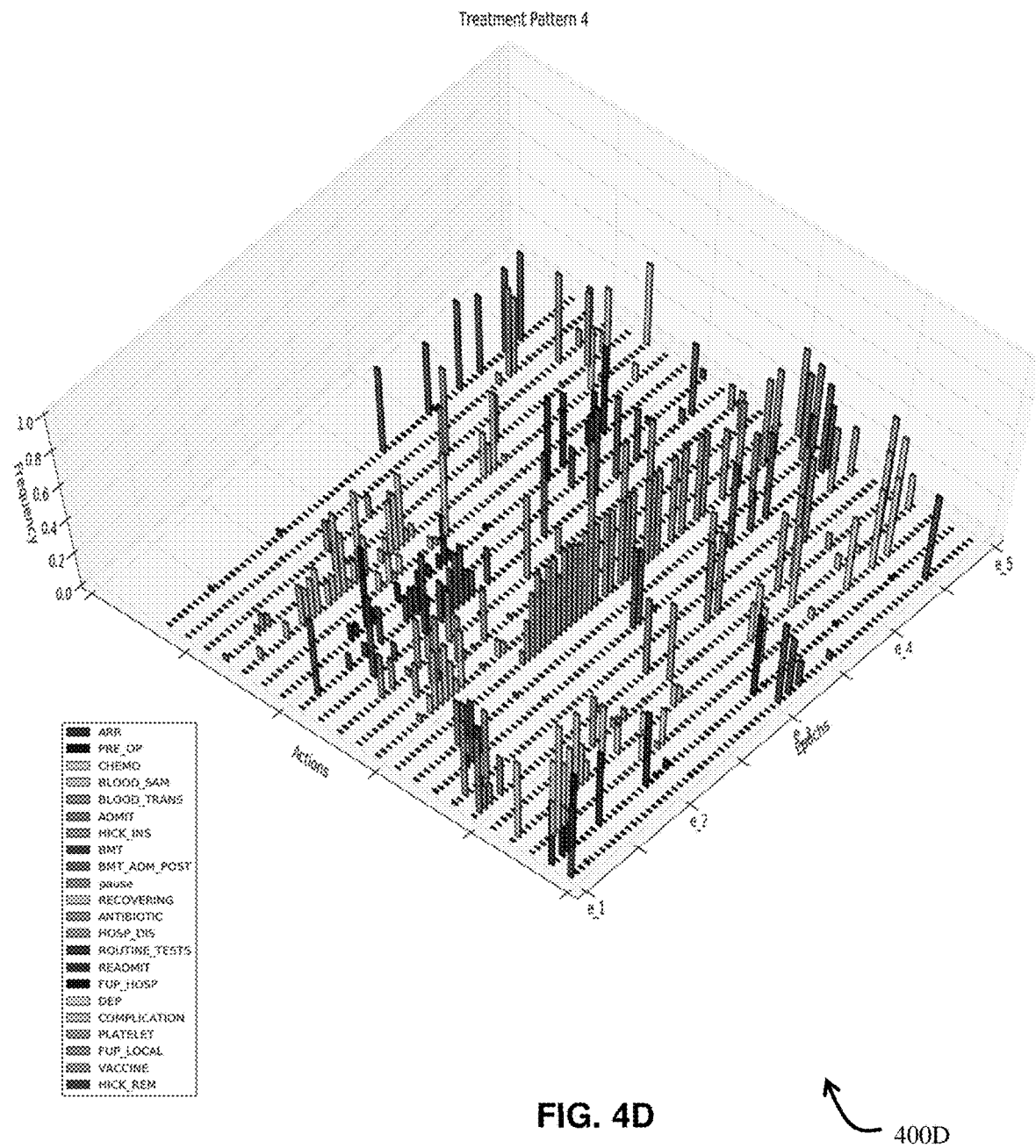

The concept of clustering is shown in FIG. 3 where the treatment topics are shown as $\sigma_1$-$\sigma_n$ (320) and their clusters are shown as $C_1$-$C_k$ (360). Each "document" (patient trace) is a superposition of treatment patterns. The "weights" of each treatment pattern is represented by $\theta_{ij}$, where the row "i" corresponds to the document and the column "j" corresponds to the treatment pattern. A "treatment pattern" is a representative treatment path that represents (more or less) how a larger group of treatment paths behave (and how historic patient trace data behaved). The clustering can be a k-means (or nearest neighbor) clustering with a "metric" defined as a function of the $\theta_{ij}$. In one example embodiment, Bayesian inference is used to extract the weights $\theta_{ij}$, (the probabilistic model calculations may be performed with a software program such as "BUGS" wrapped in python (as pyjags)).

"Clustering" is grouping of historical patient treatments (patient traces) according to their similarities. These similarities refer to the "treatment pattern composition" similarity. E.g. (assuming we have 4 treatment patterns: A, B, C and D) we can have patients traces (pt):

a) pt_1=[11% pattern A, 22% pattern B, 24% pattern C, 43% pattern D]
b) pt_2=[9% pattern A, 23% pattern B, 27% pattern C, 41% pattern D]
c) pt_3=[12% pattern A, 21% pattern B, 25% pattern C, 42% pattern D]
...
d) pt_4=[67% pattern A, 13% pattern B, 10% pattern C, 10% pattern D]
e) pt_5=[70% pattern A, 15% pattern B, 8% pattern C, 7% pattern D]
f) pt_6=[60% pattern A, 17% pattern B, 12% pattern C, 11% pattern D]

Obviously, pt_1, pt_2 and pt_3 are similar to each other and also pt_4, pt_5 and pt_6 are also similar to each other. Then patient traces pt_1, pt_2 and pt_3 are more likely that they will cluster in the same cluster (let's call that "cluster 1") and also pt_4, pt_5 and pt_6 are also likely that they will cluster together in another cluster (let's call that "cluster 2").

Given these clusters, centroids may be determined. For example, assuming four (4) treatment patterns, one centroid may look like:

$$C1=(0.6*PatternA, 0.3*PatternB, 0.05*PatternC, 0.05*PatternD)$$

The interpretation is that historical treatment paths clustered by similarity may be used to assess the probability that the given treatment path produced the desired result.

With the above, all data that cluster around C1 are of a similar treatment path. Therefore, the solution associates the "centroid" with the "treatment path". Each one of the clusters (as a result of the clustering as described above) has a patient trace representative or a centriod. A simple approach is to just take the "average" within each cluster. For example the representatives of "cluster 1" and "cluster 2" above would be:

$$C1\ rep=[32/3\%\ patternA, 66/3\%\ patternB, 76/3\%\ patternC, 126/3\%\ patternD]$$

$$C2\ rep=[197/3\%\ patternA, 45/3\%\ patternB, 30/3\%\ patternC, 28/3\%\ patternD]$$

The cluster representatives themselves represent a pattern combination that can have the following interpretation for cluster 1:

a) If a "patient trace" belongs to "cluster 1" that implies that if we follow pattern D, then the highest probability (that is 126/3=42%) of having the desirable outcome is obtained by following pattern D (without knowing anything about the individual patient).

b) The second highest probability is pattern C with probability of desirable outcome being 25.33% without knowing anything about the individual patient.

Each treatment path cluster is defined by its "centroid":

$$\sigma_{c_i} = \{[a_1, t_1], [a_2, t_2], \ldots, [a_j, t_j], \ldots [a_T t_T]\}.$$

Note that there are two possible representations of the data and centroids: one is the "original form":

$$\{[a_1, t_1], [a_2, t_2], \ldots, [a_j, t_j], \ldots [a_T t_T]\}$$

and the other one is the representation of data according to their "treatment pattern content" in a "treatment pattern content" form such as:

(20% patternA, 30% patternB, 15% patternC, 35% patternD).

We can go back and forth from one representation to the other depending on what the question is. At the stage when we perform clustering according to the treatment pattern content, all data are in the treatment pattern content form. Therefore, at that stage the centroids will also be in the treatment pattern content form. However, we have a 1-to-1 mapping from one form to the other so we can express centroids either as treatment pattern content form or as the original form (depending on what the question is). Recommendations and output to a physician can be made using either format which may reflect the choice of the physician.

e. An Example Embodiment of Building Binary Classifiers

Referring to FIG. 2 and the step of building and training the binary classifiers at 240, one example embodiment is illustrated below.

As described above, one goal of these methods and systems is to identify what treatment path to follow when a new patient is admitted for treatment such that the treatment path can be targeted to a selected outcome. For example, target outcomes may be:

a) Better (i.e. the outcome is better or more positive)
b) Faster (i.e. results are achieved faster)
c) Cheaper (i.e. results are achieved at a lower cost)

Therefore, a set of labeled patient trace data (labeled as positive/negative, slow/fast, cheap/expensive) is needed to discover a "map" that associates data from each historic patient to each one of the three treatment outcomes (outcome, speed, cost). In one embodiment, for each outcome (outcome, speed, cost) 'labels' are associated with the two extremes. For example, for a fast outcome we may associate label '1' and for slow outcome we may associate label '0'.

Binary classifiers are very powerful tools for discovering such associations. Effectively, binary classifiers perform a multidimensional (non-linear) regression analysis. The output of many binary classification algorithms is a prediction score that indicates the certainty that the given observation belongs to the positive class. In the example embodiments discussed, the binary classifiers provide a prediction (e.g., probability) whether the treatment fits into the classes of being better, faster and cheaper. Note that the classifiers usually discover a very complicated (non-linear) association that does not really need to be "visible" i.e. we may not be able to verbalize what factors are participating (and in what exact manner) at making the chosen treatment path better, faster and cheaper. One example of a suitable binary classifier is "Support Vector Machine".

In one example embodiment, binary classification is made on labelling of positive vs negative, slow vs fast, cheap vs expensive. In this embodiment, each historical treatment path/patient data pair ("patient+treatment") is defined by a series of new patient data characteristics ($d_i$), and the corresponding "patient trace data" ($\sigma_i$) followed during the historical treatment. Therefore, we define each "patient+treatment" by: $PT_i = [d_i, \sigma_i]$. In this embodiment, patient information, $d_i$, is considered as "fixed" (i.e. the hospital cannot change that), however, the patient trace or treatment path, $\sigma_i$, is a "variable" and the hospital can choose what $\sigma_i$ to follow as a treatment path according to the patient.

Therefore, the classification problem can be defined as: "Given a patient's information $d_i$, what patient trace or treatment path $\sigma_{Ci}$ (i.e. what treatment path cluster as defined above) should the hospital follow to make the $PT_i = [d_i, \sigma_i]$ pair more likely to map to treatment targets such as "positive", "fast" or "cheap"?

For each one of the treatment outcomes we "train" a binary classifier, a support vector machine (SVM) or an artificial neural network (ANN). "Training" means discovering associations that will enable us to predict whether each new patient "patient+treatment" ($PT_i = [d_i, \sigma_i]$) will result in a positive outcome (first binary classifier), or a fast outcome (second binary classifier) or a cheap outcome (third binary classifier).

The binary classifiers will provide us with associations (or "mappings"):

a) $PT_i = [d_i, \sigma_i]$----(outcome)→higher is positive and lesser is negative
b) $PT_i = [d_i, \sigma_i]$----(speed)→higher is fast and lesser is slow
c) $PT_i = [d_i, \sigma_i]$----(cost)→higher is cheaper and lesser is expensive The values the binary classifiers output in "a", "b" and "c" above are probability values: The higher the value is in "a" the higher the probability the outcome will be positive, the higher the value is in "b" the higher the probability, the treatment will be fast and the higher the value is in "c" the higher the probability the treatment will be cheap.

The number of binary classifiers is based on the number of outcomes we need to optimize. For example, to optimize outcomes for speed, results and costs 3 binary classifiers are used. Any number of binary classifiers may be used.

f. An Example Embodiment of Applying the Models

Referring to FIG. 2, to apply the binary classifiers at 266, the new patient's data $d_i$ is paired with each one of the patient treatment path centriods $\sigma_{Ci}$ and the binary classifiers are used to predict the probability of the pair to match outcomes such as (a) a positive outcome, (b) fast outcome and (c) a cheap outcome. For example, we calculate:

(a) Positive vs Negative outcome:

$$PT_{i1} = [d_i, \sigma_{i1}]\text{----(outcome)} \rightarrow p_1$$

$$PT_{i2} = [d_i, \sigma_{i2}]\text{----(outcome)} \rightarrow p_2$$

. . .

$$PT_{ij} = [d_i, \sigma_{ij}]\text{----(outcome)} \rightarrow p_j$$

. . .

$$PT_{iK} = [d_i, \sigma_{iK}]\text{----(outcome)} \rightarrow p_K$$

(b) Fast vs Slow treatment:

$$PT_{i1}=[d_i,\sigma_{i1}]\text{----(speed)}\rightarrow q_1$$

$$PT_{i2}=[d_i,\sigma_{i2}]\text{----(speed)}\rightarrow q_2$$

. . .

$$PT_{ij}=[d_i,\sigma_{ij}]\text{----(speed)}\rightarrow q_j$$

. . .

$$PT_{iK}=[d_i,\sigma_{iK}]\text{----(speed)}\rightarrow q_K$$

(c) Inexpensive vs Expensive treatment:

$$PT_{i1}=[d_i,\sigma_{i1}]\text{----(cost)}\rightarrow r_1$$

$$PT_{i2}=[d_i,\sigma_{i2}]\text{----(cost)}\rightarrow r_2$$

. . .

$$PT_{ij}=[d_i,\sigma_{ij}]\text{----(cost)}\rightarrow r_j$$

. . .

$$PT_{iK}=[d_i,\sigma_{iK}]\text{----(cost)}\rightarrow r_K$$

At 268, we identify the optimum treatment path for the target outcome by selecting the PT pair that has the highest probability for that target outcome. Using the above examples: if we want to maximize the probability that the outcome is the best then we choose the treatment path $\sigma_{ij}$ that results in the highest $p_j$; if we want to maximize the probability that the speed is the highest then we choose the treatment path $\sigma_{ij}$ that results in the highest $q_j$; and if we want to maximize the probability that the cost is the lowest then we choose the treatment path $\sigma_{ij}$ that results in the highest $r_j$.

Using the example above of "cluster 1":

$$C\_1\ \text{rep}=[32/3\%\ \text{pattern}A, 66/3\%\ \text{pattern}B, 76/3\%\ \text{pattern}C, 126/3\%\ \text{pattern}D]$$

The system may then present or recommend that the best treatment path for the patient would be to follow a patient treatment path of patternD or a hybrid version of patternD and patternC.

Furthermore, the system may also present or recommend the treatment path as a treatment path centriod in the "original form" (shown below) that may represent a more traditional format of performing a series of clinical activities over a particular time:

$$\{[a_1,t_1],[a_2,t_2],\ldots,[a_j,t_j],\ldots [a_T,t_T]\}.$$

g. An Example Embodiment of Inputs, Outputs and Potential Applications

FIG. 1 similarly illustrates an example embodiment of the general methods disclosed above. Historical data 112 is used to build mathematical models such as centroids 120 and binary classifiers 140 that are later applied at 166. The application of the models at 166 also include new patient data 162 and a selection of a target for an optimum treatment path at 164. The result of the application of the models at 166 is a prediction of an optimum treatment path for the patient selected given the binary classifiers, the treatment path cluster centroids and the new patient data.

As shown in FIG. 1, the new patient data or current data may be provided by sensors such as 102B which may be a real-time sensor. Historical data may also have been collected with sensors 102A. The sensors 102A and 102B may include sensors that provide up to date or real-time data consistent with the historical data used to build the data models. For example only and not for limitation, suitable sensors 102A and 102B may include physiological, vital sign, body movement, organic substance or other medical sensors. Physiological sensors may be used to capture physiological indices of stress/emotion such as electroencephalograms (EEGs), respiration rate monitors, skin conductance response (SCR) monitors, surface skin temperature thermistor and accelerometers for motion sensing. Other medical sensors may include physical, chemical, or biological sensors to detect medical data such as but not limited to detecting glucose levels, insulin levels, pulse rate, blood pressure, blood oxygen levels, body temperature, blood cell count or respiration rate. The sensors 102A and 102B may be have various placements in relation to the patient such as in their clothing, a subcutaneous implant, a body part accessory, etc.

As shown, the output from the systems and methods may be communicated to or provided to a user interface 190 to be presented to a user. The output may be utilized as a diagnostic tool to aid in identifying and managing a myriad of medical situations. The user interface 190 may be a common user interface such as a graphic interface on a computer or tablet monitor. The user interface 190 may also be a specifically programmed processor based device. These devices have the opportunity to meet the patients' needs by administering information in real-time to interfaces such as the patient's smartphone, computer or other wireless devices and has the potential to influence their behaviors.

Figure 6:
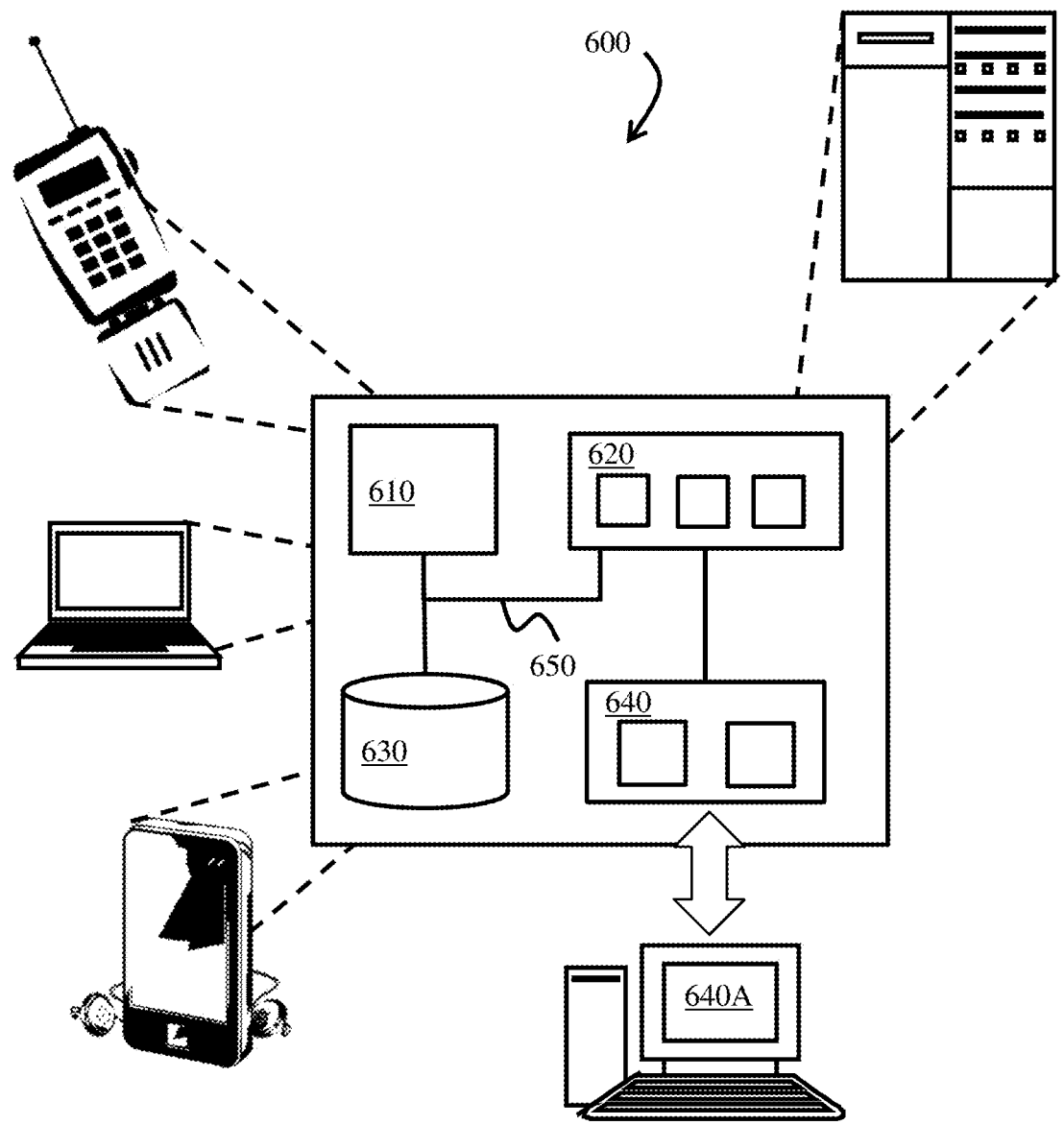
FIG. 6 illustrates one example embodiment of a computer system suitable for a treatment path selection system.

II. One Embodiment of a System to Automatically Select Treatment Paths:

The various method embodiments of the treatment path selection system may be generally implemented by a computer executing a sequence of program instructions for carrying out the steps of the methods, assuming all required data for processing is accessible to the computer, which sequence of program instructions may be embodied in a computer program product comprising media storing transitory and non-transitory embodiments of the program instructions. One example of a computer-based dynamic process modeling assembly is depicted in FIG. 6 herein by which the method of the present invention may be carried out. One embodiment of the assembly includes a processing unit, which houses a processor, memory and other systems components that implement a processing system or computer that may execute a computer program product comprising media, for example a compact storage medium such as a compact disc, which may be read by processing unit through disc drive, or any means known to the skilled artisan for providing the computer program product to the processing system for execution thereby.

The computer program may also be stored on hard disk drives within processing unit or may be located on a remote system such as a server, coupled to processing unit, via a network interface, such as an Ethernet interface. The monitor, mouse and keyboard can be coupled to processing unit through an input receiver or an output transmitter, to provide user interaction. The scanner and printer can be provided for document input and output. The printer can be coupled to processing unit via a network connection and may be coupled directly to the processing unit. The scanner can be coupled to processing unit directly but it should be understood that peripherals may be network coupled or direct coupled without affecting the ability of workstation computer to perform the method of the invention.

As will be readily apparent to those skilled in the art, the present invention can be realized in hardware, software, or a combination of hardware and software.

The present invention, or aspects of the invention, can also be embodied in a computer program product, which comprises all the respective features enabling the implementation of the methods described herein, and which, when loaded in a computer system, is able to carry out these methods. Computer program, software program, program, or software, in the present context mean any expression, in any language, code or notation, of a set of instructions intended to cause a system having an information processing capability to perform a particular function either directly or after either or both of the following: (a) conversion to another language, code or notation; and/or reproduction in a different material form.

FIG. 6 is a schematic diagram of one embodiment of a generic computer system 600. The system 600 can be used for the operations described in association with any of the computer-implemented methods described herein. The system 600 includes a processor 610, a memory 620, a storage device 630, and an input/output device 640. Each of the components 610, 620, 630, and 640 are interconnected using a system bus 650. The processor 610 is capable of processing instructions for execution within the system 600. In one implementation, the processor 610 is a single-threaded processor. In another implementation, the processor 610 is a multi-threaded processor. The processor 610 is capable of processing instructions stored in the memory 620 or on the storage device 630 to display information for a user interface on the input/output device 640.

The memory 620 stores information within the system 600. In some implementations, the memory 620 is a computer-readable storage medium. In one implementation, the memory 620 is a volatile memory unit. In another implementation, the memory 620 is a non-volatile memory unit.

The storage device 630 is capable of providing mass storage for the system 600. In some implementation, the storage device 630 is a computer-readable storage medium. In various different implementations, the storage device 630 may be a floppy disk device, a hard disk device, an optical disk device, or a tape device.

The input/output device 640 provides input/output operations for the system 600 and may be in communication with a user interface 640A as shown. In one implementation, the input/output device 640 includes a keyboard and/or pointing device. In another implementation, the input/output device 640 includes a display unit for displaying graphical user interfaces.

The features described can be implemented in digital electronic circuitry, or in computer hardware, firmware, software, or in combinations of them such as but not limited to digital phone, cellular phones, laptop computers, desktop computers, digital assistants, servers or server/client systems. An apparatus can be implemented in a computer program product tangibly embodied in a machine-readable storage device, for execution by a programmable processor; and method steps can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a computer program of instructions include, by way of example, both general and special purpose microprocessors, and a sole processor or one of multiple processors of any kind of computer. Generally, a processor will receive instructions and data from a read-only memory or a random access memory or both. The elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube), LCD (liquid crystal display) or Plasma monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

Figure 7:
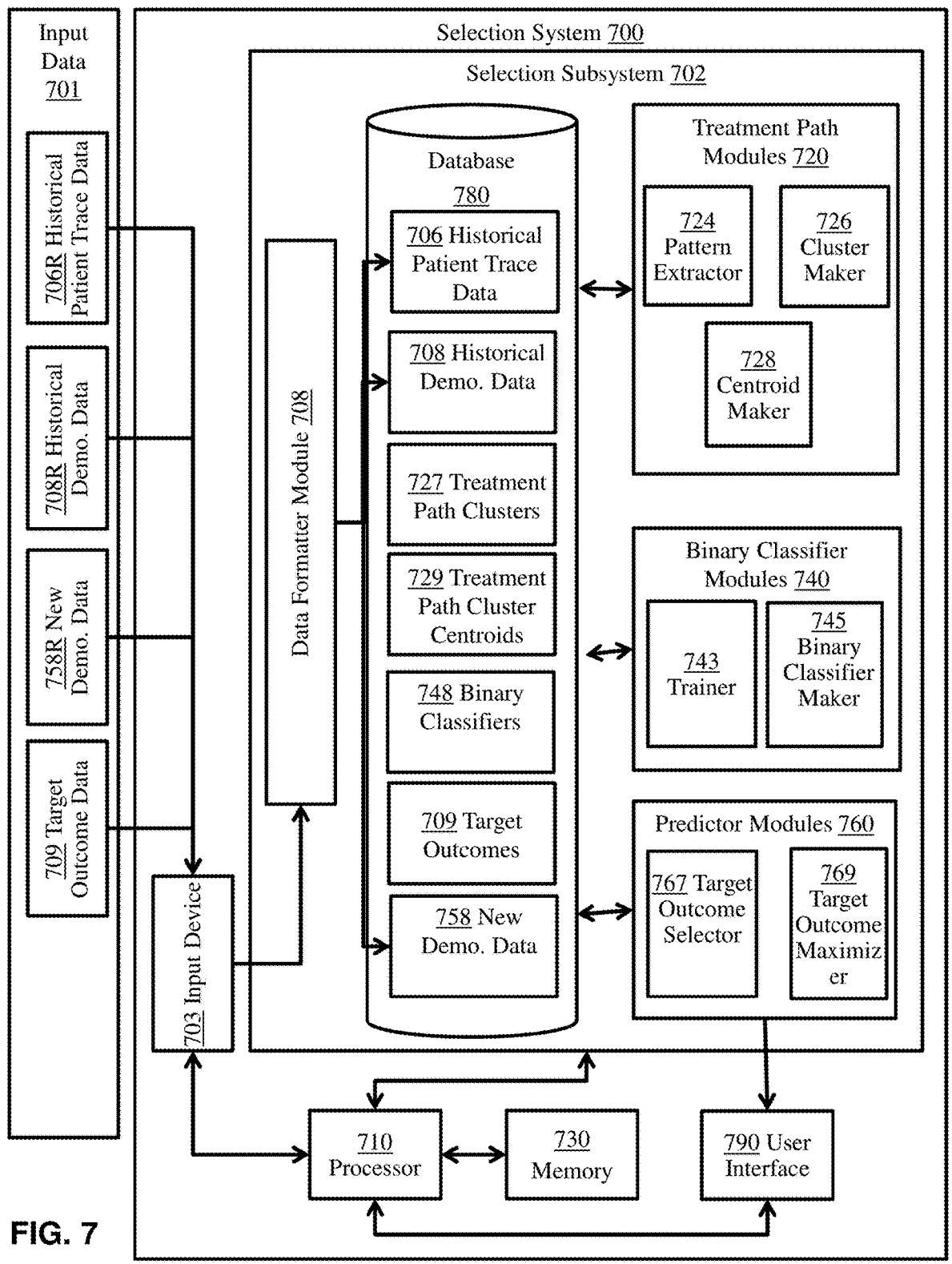
FIG. 7 illustrates a functional diagram of one embodiment of a program product capable of providing the methods of selecting treatment paths with binary classifiers.

A functional diagram of one embodiment of a specialized health care system for selecting a treatment path for a patient, including a computer program capable of executing the described methods is shown in the functional diagram in FIG. 7. As shown, the specialized health care system 700 generally comprises an input device 703, a selection subsystem 702 having various modules and a database 780, a user interface 790, a memory 730 and a processor 710. The system 700 receives various data inputs 701. The data inputs 701 may include raw data such as raw historical patient trace data 706R and raw historical patient data 708R. The data inputs 701 may also include data such as target outcome data 709. Input data 701 is generally received by the input deice 703 to be communicated to the selection system 702. For input data 701 that needs to be formatted, the data formatter module 708 formats the data from input sources to include sensor sources. Once formatted, the data is able to be put into a database 780.

Within the selection subsystem 702, the treatment path modules 720 are able to receive the data from the database 780 and perform the methods described above to include extracting topics, creating clusters and creating centroids. Generally, these methods comprise receiving the formatted historical patient trace data 706 and using the topic extractor to create topics, using the cluster maker module 726 to create clusters and using the centroid maker module 728 to create the centroids. The resulting data from these treatment modules are then communicated to and stored in the database 780. The resulting data from the treatment path modules 720 may comprise the topics, treatment path clusters 727 and treatment path cluster centroids 729.

The binary classifier modules 740 are able to receive the data from the database 780 and perform the methods described above to include creating and training the binary classifiers 748. Generally, these modules receive the treatment path centroids 729, the formatted historical patient data 708 and target outcome data 709 to train and create the binary classifiers 748. The training may be performed by the trainer module 743 and the binary classifiers may be created by the binary classifier maker 745. The resulting data from the binary classifier modules 740 generally comprises the binary classifiers 748 that are then stored in the database 780.

The data formatter module 708 is also able to receive and format formatted or raw new patient data 758R from new patients. This new patient data 758R is received by the input device 703 and communicated to and stored in the database 780. If needed, this raw new patient data 758R is formatted by the data formatter module 708.

The predictor modules 760 are able to receive data from the database 780 and perform the methods described above. Generally, these modules receive target outcome data 709 so that a target outcome can be selected. With that selected target outcome, the target outcome maximizer module 769 receives the treatment path cluster centroids 729, the binary classifiers 748, the selected target outcome from the target outcomes 709 and the new patient data 758 to identify the target outcome that maximizes the target outcome selected. The predictor modules 760, with the selection subsystem 702 and the processor 710, are also configured to communicate the outcome of the predictor module to a user interface 790.

III. Example Embodiments of a System to Automatically Select Treatment Paths:

Referring to FIG. 7, in one example embodiment a specialized health care system for selecting a treatment path for a patient is provided, the system comprising: a processor; a first input device to receive historical patient trace data corresponding to past treatments activities applied to one or more patients; a data formatter module configured to receive and transform: the historical patient trace data into a formatted historical patient trace data, a historical patient data corresponding to the one or more patients into a formatted historical patient data, a new patient data corresponding to a new patient into a formatted new patient data; a memory configured to receive and store the formatted historical patient trace data and the formatted historical patient data; a plurality of treatment path modules comprising: a topic extractor module configured to extract topics from the formatted historical patient trace data, a cluster maker module configured to receive the topics and formatted historical patient trace data to create one or more treatment path cluster, a centroid maker module configured to create one or more treatment path cluster centroid; the memory further configured to receive and store the topics, the treatment path cluster and the treatment path cluster centroid; a binary classifier module configured to receive the formatted historical patient trace data, one or more target outcomes and the historical patient data to define and train a binary classifier; the memory further configured to receive and store the binary classifier; a plurality of predictor modules comprising: a target outcome selector configured to identify one of the target outcomes as a selected target outcome, a target outcome maximizer configured to receive the treatment path cluster centroids, the new patient data and the binary classifier to select the treatment path cluster centroid as the selected treatment path for the patient; and a user interface to present the selected treatment path.

In one embodiment, a specialized health care system for selecting a treatment path for a patient comprises a non-transient computer readable medium for causing a computer to perform the method of: determining at least one treatment path cluster centroid utilizing a treatment topic extracting algorithm given: a historical patient trace data, and a historical patient patient data; training a binary classifier given: the historical patient trace data, the historical patient data, and at least one outcome; applying the binary classifier to determine a probability of the outcome for each treatment path cluster centroid given: a new patient data, and the treatment path cluster centroid; selecting one outcome as a selected outcome; and identifying the treatment path cluster centroid with the highest probability of the outcome as the selected treatment path.

In some embodiments, the historical patient trace data, the historical patient data or the new patient data are provided by medical sensors.

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

We claim:

1. A specialized health care system for selecting a treatment path for a patient, the system comprising:
 a processor;
 a first input device to receive historical patient trace data corresponding to past treatments activities applied to one or more patients;
 the historical patient trace data comprises a plurality of treatment actions each associated with a time;
 a data formatter module configured to receive and transform:
  the historical patient trace data into a formatted historical patient trace data,
  a historical patient data corresponding to the one or more patients into a formatted historical patient data, and
  a new patient data corresponding to a new patient into a formatted historical patient data;
 a memory configured to receive and store the formatted historical patient trace data and the formatted historical patient data;

a plurality of treatment path modules comprising:
a pattern extractor module configured to extract treatment patterns from the formatted historical patient trace data,
the treatment patterns comprise a 3-dimensional array wherein:
one axis represents the plurality of treatment actions,
one axis represents the time associated with each of the plurality of treatment actions, and
one axis represents a probability of each of the plurality of treatment actions at the time;
a cluster maker module configured to create one or more treatment path cluster given the formatted historical patient trace data and the treatment patterns, and
a centroid maker module configured to create one or more treatment path cluster centroid;
the memory further configured to receive and store the one or more treatment path cluster and the one or more treatment path cluster centroid;
a binary classifier module configured to receive the formatted historical patient trace data, one or more target outcomes and the historical patient data to define and train a binary classifier;
the memory further configured to receive and store the binary classifier;
a plurality of predictor modules comprising:
a target outcome selector configured to identify a selected target outcome, and
a target outcome maximizer configured to receive the one or more treatment path cluster centroid, the new patient data and the binary classifier to select one of the one or more treatment path cluster centroid as a selected treatment path for the patient; and
a user interface to present the selected treatment path.

2. The specialized health care system of claim 1 wherein:
the pattern extractor module is configured to extract treatment patterns from the formatted historical patient trace data utilizing an extended Latent Dirichlet Allocation method; and
the treatment patterns further comprise latent treatment patterns of the plurality of treatment actions.

3. The specialized health care system of claim 1 wherein the cluster maker module is configured to create one or more treatment path cluster given the formatted historical patient trace data and the treatment patterns utilizing a probabilistic method.

4. The specialized health care system of claim 1 wherein the new patient data is provided by medical sensors.

5. The specialized health care system of claim 1 wherein the formatted historical patient trace data comprises a plurality of treatment actions each associated with a time.

6. The specialized health care system of claim 1 wherein:
the binary classifier maps each historical patient trace data and each treatment pattern to a probability of one of a binary result; and
the target outcome maximizer configured to select the treatment pattern with the highest probability as the selected treatment path for the patient.

7. The specialized health care system of claim 1 wherein:
the binary classifier maps the historical patient trace data to each treatment pattern to a probability of one of a binary result;
the one or more treatment path cluster centroid comprises a treatment pattern combination; and
the target outcome maximizer configured to select one of the one or more treatment path cluster centroid with the highest probability as the selected treatment path for the patient.

8. The specialized health care system of claim 1 wherein the binary classifier defines a probability of an expensive treatment versus an inexpensive treatment.

9. The specialized health care system of claim 1 wherein the binary classifier defines a probability of a slow treatment versus a fast treatment.

10. The specialized health care system of claim 1 wherein the one or more treatment path cluster centroid is determined based on a similarity metric for a specific patient trace $\sigma$ wherein a treatment pattern distribution is defined as:

$$\vec{\theta}_\sigma = \{\hat{\theta}_{\sigma,z_1}, \hat{\theta}_{\sigma,z_2}, \ldots, \hat{\theta}_{\sigma,z_k}\}$$

where $$\hat{\theta}_{\sigma,z_i}$$

is a posterior estimate of $$\hat{\theta}_{\sigma,z_i}$$

for the treatment pattern $z_i$;
and the similarity between two patient traces $\sigma$ and $\sigma^*$ can be calculated as:

$$sim(\sigma, \sigma^*) = \frac{\sum_{i=1}^{K} \hat{\theta}_{\sigma,z_i} \times \hat{\theta}_{\sigma^*,z_i}}{\sqrt{\sum_{j=1}^{K} \hat{\theta}_{\sigma,z_j}^2} \sqrt{\sum_{l=1}^{K} \hat{\theta}_{\sigma^*,z_l}^2}}.$$

11. The specialized health care system of claim 1 wherein the historical patient trace data in is a format of:

$$\sigma_i = \{e_1, e_2, \ldots, e_j \ldots e_T\};$$

wherein $$e_1 = \{[a_1,t_1],[a_2,t_1], \ldots, [a_{N_1},t_1]\}$$

$$e_2 = \{[a_1,t_2],[a_2,t_2], \ldots, [a_{N_2},t_2]\}$$

$$\ldots$$

$$e_T = \{[a_T,t_T],[a_T,t_T], \ldots, [a_{N_T},t_T]\}; \text{ and}$$

wherein $e_i$ is an $i^{th}$ epoch defined by the treatment actions $a_i$ and the time $t_i$ of the $i^{th}$ "epoch").

12. A specialized health care system for selecting a treatment path for a patient, said system comprising a non-transient computer readable medium for causing a processor based device to perform a method of:
determining at least one treatment path cluster centroid utilizing a treatment topic extracting algorithm given:
a historical patient trace data,
a historical patient patient data,
the historical patient trace data comprises a plurality of treatment actions each associated with a time, and
a plurality of treatment patterns each comprising a 3-dimensional array wherein:
one axis represents the plurality of treatment actions,
one axis represents the time associated with each of the plurality of treatment actions, and
one axis represents a probability of each of the plurality of treatment actions at the time;

training a binary classifier given:
  the historical patient trace data,
  the historical patient patient data, and
  at least one outcome;
applying the binary classifier to determine a probability of the outcome for each treatment path cluster centroid given:
  a new patient patient data, and
  the at least one treatment path cluster centroid;
selecting one outcome as a selected outcome; and
identifying one of the at least one treatment path cluster centroid with a highest probability of the outcome as the selected treatment path.

13. The specialized health care system of claim 12 wherein the at least treatment path cluster centroid is determined based on a similarity metric for a specific patient trace σ wherein a treatment pattern distribution is defined as:

$$\vec{\theta}_\sigma = \{\hat{\theta}_{\sigma, z_1}, \hat{\theta}_{\sigma, z_2}, \ldots, \hat{\theta}_{\sigma, z_k}\}$$

where $$\hat{\theta}_{\sigma, z_i}$$

is a posterior estimate of $$\hat{\theta}_{\sigma, z_i}$$

for the treatment pattern $z_i$;
and the similarity between two patient traces σ and σ* can be calculated as:

$$sim(\sigma, \sigma^*) = \frac{\sum_{i=1}^{K} \hat{\theta}_{\sigma, z_i} \times \hat{\theta}_{\sigma^*, z_i}}{\sqrt{\sum_{j=1}^{K} \hat{\theta}_{\sigma, z_j}^2} \sqrt{\sum_{l=1}^{K} \hat{\theta}_{\sigma^*, z_l}^2}}.$$

14. The specialized health care system of claim 12 wherein the historical patient trace data in is a format of:

$$\sigma_i = \{e_1, e_2, \ldots, e_j, \ldots e_T\};$$

wherein $$e_1 = \{[a_1, t_1], [a_2, t_1], \ldots, [a_{N_1}, t_1]\}$$

$$e_2 = \{[a_1, t_2], [a_2, t_2], \ldots, [a_{N_2}, t_2]\}$$

$$\ldots$$

$$e_T = \{[a_T, t_T], [a_T, t_T], \ldots, [a_{N_T}, t_T]\}; \text{ and}$$

wherein $e_i$ is an $i^{th}$ epoch defined by the treatment actions $a_i$ and the time $t_i$ of the $i^{th}$ "epoch").

15. A method of selecting a treatment path of a patient, the method comprising:
  determining at least one treatment path cluster centroid utilizing a treatment pattern extracting algorithm given:
    a historical patient trace data,
    a historical patient patient data,
    the historical patient trace data comprises a plurality of treatment actions each associated with a time, and
    a plurality of treatment patterns each comprising a 3-dimensional array wherein:
      one axis represents the plurality of treatment actions,
      one axis represents the time associated with each of the plurality of treatment actions, and
      one axis represents a probability of each of the plurality of treatment actions at the time;
  training a binary classifier given:
    the historical patient trace data,
    the historical patient patient data, and
    at least one outcome;
  applying the binary classifier to determine a probability of the outcome for each treatment path cluster centroid given:
    a new patient patient data, and
    the at least one treatment path cluster centroid;
  selecting one outcome as a selected outcome; and
  identifying one of the at least one treatment path cluster centroid with a highest probability of the outcome as the selected treatment path.

16. The method of claim 15 wherein the one or more treatment path cluster centroid is determined based on a similarity metric for a specific patient trace σ wherein a treatment pattern distribution is defined as:

$$\vec{\theta}_\sigma = \{\hat{\theta}_{\sigma, z_1}, \hat{\theta}_{\sigma, z_2}, \ldots, \hat{\theta}_{\sigma, z_k}\}$$

where $$\hat{\theta}_{\sigma, z_i}$$

is a posterior estimate of $$\hat{\theta}_{\sigma, z_i}$$

for the treatment pattern $z_i$;
and the similarity between two patient traces σ and σ* can be calculated as:

$$sim(\sigma, \sigma^*) = \frac{\sum_{i=1}^{K} \hat{\theta}_{\sigma, z_i} \times \hat{\theta}_{\sigma^*, z_i}}{\sqrt{\sum_{j=1}^{K} \hat{\theta}_{\sigma, z_j}^2} \sqrt{\sum_{l=1}^{K} \hat{\theta}_{\sigma^*, z_l}^2}}.$$

17. The method of claim 15 wherein the historical patient trace data in is a format of:

$$\sigma_i = \{e_1, e_2, \ldots, e_j, \ldots e_T\};$$

wherein $$e_1 = \{[a_1, t_1], [a_2, t_1], \ldots, [a_{N_1}, t_1]\}$$

$$e_2 = \{[a_1, t_2], [a_2, t_2], \ldots, [a_{N_2}, t_2]\}$$

$$\ldots$$

$$e_T = \{[a_T, t_T], [a_T, t_T], \ldots, [a_{N_T}, t_T]\}; \text{ and}$$

wherein $e_i$ is an $i^{th}$ epoch defined by the treatment actions $a_i$ and the time $t_i$ of the $i^{th}$ "epoch").

* * * * *